(12) United States Patent
Nagle et al.

(10) Patent No.: US 6,828,474 B2
(45) Date of Patent: Dec. 7, 2004

(54) METHOD OF GRAIN PRODUCTION FOR HETEROZYGOUS WAXY SUGARY-2 MAIZE

(75) Inventors: Barry Nagle, Carmel, IN (US); Joseph L. Emling, Fishers, IN (US); Gary Apel, St. Anne, IL (US)

(73) Assignee: National Starch & Chemical Investment Holding Corporation, New Castle, DE (US)

(*) Notice: Subject to any disclaimer, the term of this patent is extended or adjusted under 35 U.S.C. 154(b) by 213 days.

(21) Appl. No.: 10/091,253

(22) Filed: Mar. 6, 2002

(65) Prior Publication Data

US 2003/0172401 A1 Sep. 11, 2003

(51) Int. Cl.[7] .............................. A01H 1/00; A01H 1/02; A01H 1/04
(52) U.S. Cl. ...................... 800/275; 800/263; 800/266; 800/271; 800/272; 800/274; 800/320.1
(58) Field of Search ................................. 800/263, 266, 800/271, 272, 274, 275, 320.1

(56) References Cited

U.S. PATENT DOCUMENTS

| | | | |
|---|---|---|---|
| 2,328,537 A | 9/1943 | Felton et al. .................. 127/33 |
| 2,801,242 A | 7/1957 | Kerr et al. ................ 260/233.5 |
| 4,280,851 A | 7/1981 | Pitchon et al. ................. 127/33 |
| 4,428,972 A | 1/1984 | Wurzburg et al. ........... 426/578 |
| 4,465,702 A | 8/1984 | Eastman et al. ............. 426/578 |
| 5,037,929 A | 8/1991 | Rajagopalan et al. ....... 426/578 |
| 5,131,953 A | 7/1992 | Kasica et al. ................. 127/65 |
| 5,149,799 A | 9/1992 | Rubens ....................... 536/102 |
| 5,187,272 A | 2/1993 | Katcher et al. ............. 536/102 |
| 5,535,688 A | 7/1996 | Kaufman ...................... 111/52 |
| 5,675,064 A | * 10/1997 | Pearlstein et al. ........ 800/320.1 |
| 5,704,160 A | 1/1998 | Bergquist et al. .............. 47/58 |
| 5,706,603 A | 1/1998 | Bergquist et al. .............. 47/58 |
| 5,756,721 A | 5/1998 | Eden et al. ................. 536/127 |
| 5,954,883 A | 9/1999 | Nagle et al. .................. 127/36 |
| 6,218,155 B1 | 4/2001 | Chang et al. ............... 435/101 |
| 6,274,792 B1 | 8/2001 | Chang et al. ............... 800/298 |

FOREIGN PATENT DOCUMENTS

| | | |
|---|---|---|
| EP | 0 572 412 B1 | 5/1997 |
| WO | WO 95/04082 | 2/1995 |
| WO | WO 95/35026 | 12/1995 |

OTHER PUBLICATIONS

Sprague, G.F. et al, "Corn Breeding", Corn and Corn Improvement—Agronomy Monograph No. 18, 1988, pp. 305–362.

Wych, Robert D., "Production of Hybrid Seed Corn", Corn and Corn Improvement—Agronomy Monograph, 1988, pp. 561–607.

Palagyl, A. et al, "Maize Hybrid Seed Production By The Mutual Random Mating Of The Parental Components", Cereal Research Communications, vol. 24, No. 3, 1996, pp. 307–316.

Handbook of Water–Soluble Gums and Resins, Edited by Robert L. Davidson, "Starch and Its Modifications" by M.W. Rutenberg, Chapter 22, pp. 22–26 thru 22–47.

STARCH: Chemistry and Technology, vol. III, Edited by Whistler et al., "Industrial Microscopy Of Starches", by Eileen Maywald Snyder, Chapter XXII, pp. 661–673.

* cited by examiner

Primary Examiner—David T. Fox
(74) Attorney, Agent, or Firm—Karen G. Kaiser

(57) ABSTRACT

This patent pertains to a method of producing a waxy maize starch derived from a plant which is heterozygous for the recessive sugary-2 allele by interplanting waxy maize seed which is homozygous for the dominant sugary-2 allele and waxy maize which is homozygous for the recessive sugary-2 allele, one hybrid being male sterile. The maize is harvested and processed together to obtain starch with excellent low temperature and freeze-thaw stability, high pasting temperature, and intact granules.

14 Claims, No Drawings

METHOD OF GRAIN PRODUCTION FOR HETEROZYGOUS WAXY SUGARY-2 MAIZE

BACKGROUND OF THE INVENTION

The present invention relates to a method of producing a waxy maize starch derived from plants and grains which are predominantly heterozygous for the recessive sugary-2 allele by interplanting waxy maize seed which is homozygous for the dominant sugary-2 allele and waxy maize seed which is homozygous for the recessive sugary-2 allele, one hybrid being male sterile. The maize is harvested and processed together to obtain starch with excellent low temperature and freeze-thaw stability, high pasting temperature, and intact granules.

Waxy maize starch which is heterozygous for the sugary-2 allele and its functionality are known in the art and disclosed in U.S. Pat. No. 5,954,883. The typical method of producing such starch is to plant such that the hybrids are alternated one male row then seven female rows. The female rows are then harvested to obtain the waxy maize hybrid which is heterozygous for the recessive sugary-2 allele. The male rows are allowed to go to waste.

This methodology is expensive with the cost of producing the waxy maize which is heterozygous for the recessive sugary-2 allele being at least 10% higher than that for waxy maize.

Surprisingly, it has now been discovered that the two hybrids may be more cost effectively produced by interplanting, harvesting and processing together the resultant hybrids without significantly losing starch functionality.

SUMMARY OF THE INVENTION

This patent pertains to a method of producing a waxy maize starch derived from plants and grain which are predominantly heterozygous for sugary-2 allele by interplanting waxy maize seed which is homozygous for the dominant sugary-2 allele and waxy maize which is homozygous for the recessive sugary-2 allele, one hybrid being male sterile. The maize is harvested and processed together to obtain starch with excellent low temperature and freeze-thaw stability, high pasting temperature, and intact granules.

F1 hybrid, as used herein, is intended to mean a hybrid arising from crossbreeding of two inbred lines.

Heterozygous, as used herein, is intended to mean a genetic condition existing when different alleles reside at corresponding loci on homologous chromosomes.

Homozygous, as used herein, is intended to mean a genetic condition existing when identical alleles reside at corresponding loci on homologous chromosomes.

Hybrid, as used herein, is intended to mean any offspring of a cross between two genetically unlike varieties.

Inbred, as used herein, is intended to mean a substantially homozygous variety.

Male sterile or female, as used herein, is intended to mean that the plant does not produce functional pollen as a consequence of any mechanism including without limitation mechanical or hand detasseling (manual), chemical sterility, or genetic sterility such as cytoplasmic male sterility which renders the tassel nonfunctional.

Unless otherwise stated, dominant genes are represented by capital letters and recessive genes by lower case letters. The endosperm of maize is triploid and contains three alleles of a gene. Thus, wxwxwxsu2su2su2 would represent a hybrid which is homozygous recessive for both the waxy gene and the sugary-2 gene while wxxwxwxSu2Su2su2 would represent a hybrid homozygous for the waxy gene and heterozygous for the sugary-2 gene with two dominant or wild alleles and one recessive or mutant allele.

DETAILED DESCRIPTION OF THE INVENTION

The present invention relates to a method of producing a waxy maize starch derived from plants and grain which are predominantly the recessive sugary-2 allele. The maize may be produced by interbreeding two hybrids, a waxy maize hybrid (wxwxwx) and a waxy maize hybrid which is homozygous recessive for the sugary-2 gene (wxwxwxsu2su2su2). The waxy maize hybrid which is homozygous recessive for the sugary-2 gene is known from U.S. Pat. No. 4,428,972.

One hybrid is rendered male sterile such that the second hybrid provides pollen for the entire field. It is irrelevant to the present invention which hybrid is chosen to be the male sterile hybrid in that either the mutant can serve as the male sterile. The particular choice of male sterile and pollinator determines the resulting genotypes of the starch derived from the two hybrids. As is known in the art, maize endosperm is triploid. The endosperm genotype has two gene doses which are inherited from the female and one gene dose which is inherited from the male. Thus, the choice of which hybrid is sterilized is made according to the desired genetic composition of the F2 grain from the F1 hybrids.

The two maize hybrids are interplanted in a field, particularly in a random fashion. The two hybrids may be planted in any ratio necessary to obtain starch with the desired functionality. Further, sufficient male fertile hybrids must be planted to pollinate the female hybrids.

A particularly suitable embodiment is when the female hybrid results in the desired starch and is planted in greater amounts than the fertile male hybrid or pollinator, particularly such that the female accounts for at least about 80%, more particularly for at least about 85%, most particularly for at least about 90% of the field. For example, if it is desired to obtain primarily waxy maize starch which is heterozygous recessive for the sugary-2 gene in two doses (wxwxwxSu2su2su2), the waxy maize hybrid homozygous recessive for the sugary-2 gene is male sterilized and interplanted with a fertile waxy maize that is homozygous dominant for the sugary-2 gene.

The F2 grains of the invention are waxy maize heterozygous for the recessive sugary-2 allele (wxwxwxSu2su2su2 or wxwxwxSu2Su2su2) with minor amounts of waxy maize which is homozygous for the dominant or recessive sugary-2 allele (wxwxwxSu2Su2Su2 or wxwxwxsu2su2su2). The two hybrids are harvested and processed together to obtain the starch by techniques known in the art, including dry milling and wet milling.

The resultant starch blend has a decreased cost of production compared to the pure F2 hybrid starch, with a premium paid to growers of less than that of producing the pure hybrid.

The resultant starch may be used as milled or converted. Conversion products derived from the present starches, including fluidity or thin-boiling starches prepared by oxidation, enzyme conversion particularly by α-amylase, acid hydrolysis, heat and or acid dextrinization, thermal and/or sheared products are also useful herein.

The starches may be modified to further enhance their properties and characteristics. Any modifications known in the art may be used, such as derivatizations to form ethers, esters or half esters such as hydroxypropyl ethers, acetates, phosphates, succinates, i.e., octenyl succinate, tertiary and quaternary amine ethers, etc., or by any other modification techniques which produce a starch having the characteristics herein defined.

The modifications include those which are chemical, physical, or thermal. When chemical derivatizations are used, the preferred substituent groups are hydroxypropyl, phosphate or acetate groups.

The preferred chemical modification of the present starch is cross-linking. Any cross-linking agent known in the art may be employed for this purpose, including but not limited to epichlorohydrin, linear dicarboxylic acid anhydrides, citric acid acrolein, phosphorus oxychloride, adipic/acetic mixed acid anhydrides, and trimetaphosphate salts for food systems and to epichlorohydrin, linear dicarboxylic acid anhydrides, citric acid acrolein, phosphorus oxychloride, adipic/acetic mixed acid anhydrides, trimetaphosphate salts, formaldehyde, cyanuric chloride, diioscyanates, and divinyl sulfones in non-food systems. The cross-linking reaction is carried out using techniques known in the art, for example those described in U.S. Pat. Nos. 2,328,537 and 2,801,242. Procedures for modifying starches are described in the Chapter "Starch and Its Modification" by M. W. Rutenberg, pages 22–26 to 22–47, Handbook of Water Soluble Gums and Resins, R. L. Davidson, Editor (McGraw-Hill, Inc., New York, N.Y. 1980).

The amount of cross-linking agent necessary to give a suitable product is well known in the art and will vary depending, inter alia, on the type of cross-linking agent employed, the concentration of the cross-linking agent, the reaction conditions, and the necessity for having a cross-linked starch. Typically, this amount will range from about 0.001 to about 10.0% by weight of the starch.

The present starches may also be physically modified, such as by thermal inhibition described in WO 95/04082 (published Feb. 9, 1995).

The starches may also be pregelatinized. Exemplary processes for preparing pregelatinized starches are disclosed in U.S. Pat. No. 4,280,851 (Pitchon, et al.), U.S. Pat. No. 4,465,702 (Eastman, et al.), U.S. Pat. No. 5,037,929 (Rajagopalan), U.S. Pat. No. 5,131,953 (Kasica, et al.), and U.S. Pat. No. 5,149,799 (Rubens). Conventional procedures for pregelatinizing starch are well known to those skilled in the art and described in such articles as Chapter XXII— "Production and Use of Pregelatinized Starch", Starch: Chemistry and Technology, Vol. III—Industrial Aspects, R. L. Whistler and E. F. Paschall, Editors, Academic Press, New York 1967.

The present starches may be purified by any method known in the art to remove off-flavors and colors that are native to the starch or created during starch modification processes. Purification processes preferred for treating the present starches are disclosed in U.S. Ser. No. 07/832,838 filed Feb. 7, 1992, by Kasica, et al. Alkali washing techniques, for starches intended for use in either granular or pregelatinized form, are also useful and described in the family of patents represented by U.S. Pat. No. 5,187,272 (Bertalan, et al.).

The valuable functionality of the present maize starch include excellent low temperature and freeze-thaw stability, a relatively high peak viscosity, a relatively high pasting temperature, and large, uniformly sound intact granules.

The starches may be used in a variety of industrial products including, without limitation, food and beverages, pharmaceuticals, paper and paper products, delivery systems such as emulsifiers and encapsulating agents, cosmetic products, detergents and personal care products. Of particularly importance is in food and beverage products in which the product is exposed to prolonged storage at relatively low temperatures, including freezing temperatures, and/or exposure to repeated freezing and thawing cycles. This includes without limitation canned and frozen products such as pies, soups, and the like. Use of the present starches in such applications will allow the food products to retain their quality by retarding syneresis and marked deterioration of product texture, color and clarity.

The present starches can be used in products as a direct replacement for chemically modified starch. The starch may be added in an amount effective to provide the same functionality as the chemically modified starch. In general, the present starches are added in an amount of from about 0.1 to about 20% by weight of the product, either directly or by adding a slurry or sol containing the starch to the product.

EXAMPLES

The following examples are presented to further illustrate and explain the present invention and should not be taken as limiting in any regard. All percents used are on a weight/weight basis.

The following methods were used throughout the examples.

Bath Cook

Starch samples were bath cooked at 95° C. for 20 minutes at 5% solids. The starch slurry was mixed with a glass rod for three minutes followed by quiescent heating for 17 minutes. The concentration of the cook was maintained by compensating for evaporation during the bath cooking.

Freeze-Thaw Stability Test

The bath cooked starches were cooled to room temperature, then poured into 4 oz. (0.55 kg) jars and placed in a deep freezer (–19° C.) for 16 hours. The samples were then removed from the freezer and thawed for 8 hours at room temperature. The samples were visually inspected for syneresis, both on the surface and when pressed, as well as for opacity and gelling changes. This freeze-thaw cycle was repeated until two of the four properties failed for the sample.

Example 1

Production of Waxy Maize with One or Two Doses of the Sugary-2 Gene

A. A male sterile mutant of waxy/sugary-2 (wxwxwxsu$_2$su$_2$su$_2$) and a male fertile mutant of waxy (wxwxwx) are randomly interplanted in a field in a ratio of 90:10 (sterile:fertile). The seeds are harvested together, resulting in a blend of approximately 10% waxy maize (wxwxwx) and 90% waxy maize with two doses of recessive sugary-2 gene (wxwxwxSu2su2su2).

B. A male fertile mutant of waxy/sugary-2 (wxwxwxsu2su2su2) and a male sterile mutant of waxy (wxwxwx) are randomly interplanted in a field in a ratio of 90:10 (sterile:fertile). The seeds are harvested together, resulting in a blend of approximately 90% waxy maize with one dose of recessive sugary-2 (wxwxwxSu2Su2su2) and 10% waxy corn with three doses of recessive sugary-2 (wxwxwxsu2su2su2).

C. Example 1A was repeated with a hybrid ratio of 80:20 (sterile:fertile) to produce a blend of approximately 20% waxy maize (wxwxwx) and 80% waxy maize with two doses of recessive sugary-2 gene (wxwxwxSu$_2$su$_2$su$_2$).

Example 2

Freeze-Thaw Stability Comparison

The freeze thaw stability of several starches were compared. The results are shown in Table 1, below. Each number represents the number of freeze-thaw cycles the starch cook remained acceptable (stable).

1A=The starch of Example 1A.

1C=The starch of Example 1C

Waxy=Pure waxy maize homozygous for the dominant sugary-2 gene (wxwxwxSu2Su2Su2)

2DOSE=Pure waxy maize hybrid with two doses of recessive sugary-2 gene (wxwxwx$Su_2su_2su_2$)

TABLE 1

Freeze-thaw Stability

| Starch | Opacity | Gelling | Syneresis (surface) | Syneresis (pressed) | Overall Stability |
|---|---|---|---|---|---|
| 1A | 3 | 3 | 3 | 3 | 3 |
| 1C | 2 | 2 | 2 | 2 | 2 |
| Waxy | <1 | <1 | <1 | <1 | <1 |
| 2DOSE | 3 | 3 | 3 | 3 | 3 |

As can be seen from Table 1, the 90:10 blend of the present invention performed as well as the pure hybrid. While the 80:20 blend of the present invention did not perform quite as well, it still was substantially superior to waxy maize.

We claim:

1. A method of planting comprising the steps of:
   (a) interplanting two hybrids, wherein:
      (1) the first hybrid is a male fertile waxy maize seed; and
      (2) the second hybrid is a male sterile waxy maize seed which is homozygous recessive for the sugary-2 allele;
   (b) permitting the male fertile maize plants to pollinate said male sterile maize plants; and
   (c) harvesting the resulting maize seed from the two hybrids together to result in a blend.

2. The method of claim 1, wherein the maize plants have been rendered male sterile by cytoplasmic, genetic, mechanical, chemical, manual, or a combination of such methods.

3. The method of claim 1, wherein the hybrids are interplanted randomly.

4. The method of claim 3, wherein the male sterile hybrid is present in an amount greater than that of the male fertile hybrid.

5. The method of claim 4, wherein the planting of the hybrids is such that the male sterile accounts for at least about 80% of the hybrids.

6. The method of claim 5, wherein the planting of the hybrids is such that the male sterile accounts for at least about 85% of the hybrids.

7. The method of claim 4, wherein the planting of the hybrids is such that the male sterile accounts for at least about 90% of the hybrids.

8. A method of planting comprising the steps of:
   (a) interplanting two hybrids, wherein:
      (1) the first hybrid is a male sterile waxy maize seed; and
      (2) the second hybrid is a male fertile waxy maize seed which is homozygous recessive for the sugary-2 allele;
   (b) permitting the male fertile maize plants to pollinate said male sterile maize plants; and
   (c) harvesting the resulting maize seed from the two hybrids together to result in a blend.

9. The method of claim 8, wherein the maize plants have been rendered male sterile by cytoplasmic, genetic, mechanical, chemical, manual or a combination of such methods.

10. The method of claim 8, wherein the hybrids are interplanted randomly.

11. The method of claim 10, wherein the male sterile hybrid is present in an amount greater than that of the male fertile hybrid.

12. The method of claim 11, wherein the planting of the hybrids is such that the male sterile accounts for at least about 80% of the hybrids.

13. The method of claim 12, wherein the planting of the hybrids is such that the male sterile accounts for at least about 85% of the hybrids.

14. The method of claim 11, wherein the planting of the hybrids is such that the male sterile accounts for at least about 90% of the hybrids.

* * * * *